United States Patent [19]

Rao et al.

[11] Patent Number: 5,024,835
[45] Date of Patent: Jun. 18, 1991

[54] CONJUGATES OF A VINCA DERIVATIVE CARRYING A DETERGENT CHAIN IN THE C-3 POSITION

[75] Inventors: KSP Siva Bhushana Rao, Rosieres; Jean-Paul Dejonghe, Wawre; Marie-Paule Collard, Brussels; Andre Trouet, Winksele-Herent, all of Belgium

[73] Assignee: Ire-Celltarg S.A., Fleurus, Belgium

[21] Appl. No.: 306,639

[22] Filed: Feb. 3, 1989

[30] Foreign Application Priority Data

Feb. 8, 1988 [FR] France .................................. 88 01439

[51] Int. Cl.$^5$ .................... A61K 39/44; A61K 37/36; A61K 37/04; C07K 17/00
[52] U.S. Cl. ................................. 424/85.91; 530/324; 530/363; 530/391; 530/395; 530/399; 530/409; 514/12; 514/21
[58] Field of Search ............... 530/363, 395, 399, 391, 530/324, 409; 424/85.91; 514/12, 21

[56] References Cited

U.S. PATENT DOCUMENTS 4,675,400 7/1987 Cullinan .............................. 540/478
4,828,831 5/1989 Hannart et al. .................. 424/85.91

FOREIGN PATENT DOCUMENTS 0041935 12/1981 European Pat. Off. .
0121388 10/1984 European Pat. Off. .
0124502 11/1984 European Pat. Off. .
0206667 12/1986 European Pat. Off. .
2592883 7/1987 France .
2111055 6/1983 United Kingdom .

OTHER PUBLICATIONS

Brown et al. (1978), Arch. Biochem. Biophys., 188 (2):418–428.
Rao et al. (1985), in Recent Adv. Chemother., Proc. Int. Congr. Chemother., 14th volume, Anticancer Sect. 1, Ed. Ishiganni, Univ Tokyo Press, pp. 323–324.
Teale et al. (1977), Br. J. Clin. Pharmac., 4:169–172.

Primary Examiner—Jeffrey E. Russel
Assistant Examiner—Kay Kim
Attorney, Agent, or Firm—Bertram I. Rowland; Richard L. Neeley

[57] ABSTRACT

The subject of the present invention is conjugates of vinca (indole-dihydroindole) derivatives carrying a detergent chain of at least 7 aliphatic carbon atoms in the C-3 position bonded via a covalent bond to a macromolecular carrier of polypeptide character, and also pharmaceutical compositions containing these conjugates and a process of preparation.

16 Claims, 2 Drawing Sheets

FIG_1

CONJUGATES OF A VINCA DERIVATIVE CARRYING A DETERGENT CHAIN IN THE C-3 POSITION

The present invention relates to medicament-carrier cubjugates which use as medicaments vinca alkaloids for the treatment of cancer. These drugs have the characteristic of blocking the multiplication of the tumor cells, but also that of normal cells having a high rate of division, as is the case with hematopoietic cells and epithelial cells of the intestine. Moreover, these medicaments may have a toxic effect on other tissues and are, respectively, cardiotoxic and neurotoxic.

The derivatives of vinca alkaloids most used at present are vinblastine and vincristine.

Vinblastine and vincristine are two dimer derivatives extracted from the leaves of Catharanthus Roseus. Vindesine is a hemisynthetic dimer obtained starting from vinblastine. These three derivatives are currently the most used in human medicine in the treatment of various types of cancerous diseases. This use is justified by their very clear activity against human tumors, such as Hodgkins disease, and tumors of the breast and of the lung for vinblastine, lymphosarcomas, lymphoblastic leukemia and acute transformations of chronic lymphoblastic leukemias for vincristine and vindesine. The use of these substances is, however, limited by their neurological and hematological toxicity. A research program has been underway for several years which envisages the development of novel, less toxic derivatives of vincristine and vinblastine. Numerous derivatives of vinca alkaloids have been synthesized with the aim of obtaining more advantageous antitumor pharmacological activities. According to the invention, methods have been developed in order to couple derivatives of vinca alkaloids to macromolecular carriers with the aim, in accordance with the conceptual approach of targeting medicaments, of enabling the therapeutic activity to be increased while reducing the inherent toxicity of these medicaments. For example, a carrier which has been proposed according to the invention is galactosylated human albumin which is selectively recognized by the hepatocytes and the cells of the human hepatoma. Techniques are perfected in order to produce this neoglycoprotein under aseptic and apyrogenic conditions permitting its administration to humans. Finally, hybridomes have been created which secrete monoclonal antibodies having a high affinity and a good selectivity for the cells of the human hepatoma. Conjugation to monoclonal antibodies has also been effected.

More precisely, the present invention relates to novel conjugates of derivatives of vinca alkaloids of the indole-dihydroindole type with targeting agents.

The specificity of the approach to the problem of chemotherapy of cancers according to the invention relies on the concept of targeting medicaments which aims, in fact, to augment the selectivity of antitumor agents while coupling these to carriers recognized as specifically as possible by the cells which it is desired to affect. In addition to a greater activity resulting from the fact that almost all of the medicament administered should reach its target, this approach aims to considerably reduce the toxicity of antitumor agents. This approach is based on the type of chemical bond which is interposed between the medicament and its carrier. In fact, the bonds according to the invention are covalent, which enables the dissociation of non-covalent conjugates by the simple effect of dilution to be avoided; they have also been selected on the basis of their stability in the extracellular biological fluids and of their reversibility in the presence of lysosomal enzymes. Preferably, the medicament/carrier conjugates which have been developed must be, on the one hand, recognized by specific sites present on the surface of the tumor cells, but they must, on the other hand, be endocytosed and rejoin the lysosomes.

In the present application it is thus intended to indicate, as the targeting agent, specific macromolecular carriers selectively targeting the active substance towards the target cells to be treated. In general these carriers are proteins such as AHgal or a growth factor such as EGF or protein fragments, especially immunoglobulins or immunoglobulin fragments. For example, in the case of cancer, which is concerned here, monoclonal antibodies directed against the antigens associated with tumors are particularly suitable.

As has been mentioned above, the targeting systems or conjugates involved in the present invention require, in addition to the targeting agent and the active substance, the presence of a covalent chemical bond between these two compounds. This can be a bond between a terminal chemical group of the active substance and a complementary chemical group of the targeting agent, for example COOH and $NH_2$. It may also be a chemical grouping or branch ensuring the link between the two compounds.

The description of the characteristics which the various elements involved in the concept of targeting must have will be found in patent application FR-85 10 234 filed by the Applicant.

The derivatives of vinca alkaloids have been the subject of numerous investigations, studies and patents with the preparation in view of substances which are more active, more selective and less toxic as anti-tumor agent, in the form of conjugates.

Up to now, the coupling of indole-dihydroindole dimers to a protein has been envisaged essentially according to two routes.

1) Coupling in the C-4 position
  a) via an ester group derived from the hydroxyl group on the carbon in the 4-position of the vinca alkaloid skeleton (European Patent Application EP-124 502). This thus involved coupling vindesine via a hemisuccinate branch to an immunoglobulin.
  b) Via a bifunctional organic derivative of the maleoylamino acid type, especially Ala-Mal in Luxembourg Patent Application No. 86 212 in particular.

However, other C-4 couplings in accordance with these two types are found in Patent Applications EP 121 388 and EP 123 441.

2) Coupling in the C-3 position
  a) vindesine has been coupled directly to an immunoglobulin via an azide derivative in European Patent Application EP 56 322.
  b) Applications EP 206 666 and EP 206 667 also propose couplings of vinblastine hydrazide bonded via a branch of the hemisuccinate type to an immunoglobulin.

The present invention proposes obtaining novel conjugates of derivatives of vinca alkaloids starting from novel derivatives described in Patent Applications FR 86 000 364 and FR 86 17 412 filed by the Applicant.

In fact, the subject of the present invention is conjugates of vinca (indole-dihydroindole) derivatives carrying a detergent chain of at least 7 aliphatic carbon atoms in the C-3 position bonded via a covalent bond to a macromolecular carrier of polypeptide character.

More particularly, the subject of the present invention is conjugates of a vinca (indole-dihydroindole) alkaloid derivative carrying a detergent chain of at least 7 aliphatic carbon atoms in the C-3 position, the said chain being substituted at its end by a COOH radical coupled to a free amino group of a macromolecular carrier of polypeptide character via an amide (-CONH-) bond.

More particularly, the conjugates which have the formula I

(I)

in which:

($R_1$, $R_2$) represent (—Et, —OH) or (—H, Et)
$R_4$ represents —H, —Me or —CHO,
$R_3$ represents —OH or

R represents

A being chosen from amongst —NH—, and or A is the divalent radical of an amino acid entering into the structure of proteins terminating by —NH and or —NH and alk denotes a straight or branched $C_1$ to $C_7$ divalent hydrocarbon chain, R' represents an aliphatic hydrocarbon radical having at least 7 aliphatic carbon atoms,

R is substituted by a radical originating from a terminal —COOH radical of R' coupled to a free amino group of the carrier T via a bond, —R—T thus being able to be represented by where —T=—NH—P.

Amongst the aliphatic hydrocarbon radicals, the radicals:
straight-chain or branched $C_1$ to $C_{20}$ alkyl and
straight-chain or branched $C_1$ to $C_{20}$ alkenyl may be mentioned, these radicals preferably being straight-chain; when these radicals are substituted they are preferably substituted at the end of the chain.

Amongst the alk radicals, there may be mentioned the straight-chain or branched $C_1$ to $C_7$, preferably $C_1$ to $C_5$ hydrocarbon radicals which are unsubstituted or substituted by one or more radicals OH, $NH_2$ or COOH.

When A is a divalent radical of an amino acid entering into the structure of proteins, it may be in the D form or in the L form when it carries an asymmetric carbon atom.

The radical A may originate from Gly, Ala, Val, Leu, Ile, Phe, Ser, Thr, Lys, Lys-OH, Arg, Asp, Asp-$NH_2$, Glu, Glu-$NH_2$, Cys-SH, Met, Tyr, Trp or His, but preferably Ala.

When these radicals occur as groups other than bonding groups, they may be protected by protective groups known in protein chemistry, such as the Cbz (carbobenzyloxy) group for example.

The conjugates for which
$R_3$=—OH and
A=—NH— may be mentioned in particular.

Amongst the conjugates of the formula I, the conjugates in which
($R_1$, $R_2$)=(—Et, —OH) and $R_4$=Me may also be mentioned more particularly.

Particularly advantageous conjugates are obtained when —A—R' is chosen from amongst —NH—$(CH_2)_{11}$, —NH—$(CH_2)_{17}$, and NH—$(CH_2)_7$—CH=CH—$(CH_2)_8$.

Preferably, the macromolecular carrier is chosen from amongst proteins, neoglycoproteins and IgG immunoglobulins or fragments of these.

Amongst the proteins or neoglycoproteins there may be mentioned:

bovine albumin serum or galactosylated human albumin and growth factors such as EGF (Epidermal Growth Factor).

In fact, two types of carriers may be mentioned in particular. Firstly, neoglycoproteins which exhibit galactose residues and which are recognized by a receptor present on the surface of the hepatocytes, but also of human hepatoma cells.

On the other hand, in the case of tumor cells, another type of carriers may be mentioned, in this case, monoclonal antibodies. This approach profits from the selectivity of the antigen/antibody reaction and is based on the hypothesis that tumor cells may exhibit more or less specific antigens on their plasmic membrane. The first antigens against which antibodies may be produced are the organotypical antigens. This permits the capture of medicament/carrier conjugates to be limited to a single cell type, but does not impede access of the conjugate to normal cells exhibiting antigens. A second type of target is made up by the antigens associated with tumors. The antigens present at the surface of embryonic cells which reappear during the malignant transformation, or antigens which are present in very small numbers on the surface of normal cells but increase considerably in number in the course of cancer development may also be included in this category. In certain cases also these are the antigens of viral origin which appear at the surface of infected and transformed cells. The third type of antigens which may be considered as a target is made up of specific antigens of tumor cells. Although this subject is still largely under discussion, it would appear that specific antigens would be able to appear during the cancerous transformation and be displayed on the surface of tumor cells. Antibodies directed against such antigens represent ideal carriers. An example of an antigen considered functionally tumor-specific is the idiotype of surface immunoglobulins carried by certain cells of leukemia B or of lymphomas.

Thus, galactosylated human albumin, which is recognized selectively by the hepatocytes and the cells of human hepatoma, may be mentioned as a carrier.

Amongst the monoclonal antibodies having a high affinity and a good selectivity for the cells of human hepatoma, antibody CT-M-01 described in Application FR 85 10 234 may also be used.

The present invention also relates to a process for the preparation of conjugates, characterized in that 1) the C-3 vinca alkaloid derivative to be coupled is prepared a) by reacting the hydrazide of the formula with a nitrite in order to form the corresponding azide in the C-3 position and b) by reacting the azide with an amine of the formula $$H-A-R'-COZ$$

the terminal COOH group of R' being protected in the form of a protective group known in Z protein chemistry, especially the benzyl group, and c) by removing the protection from the terminal COOH group of R' in the derivative obtained after step b).

2) the derivative obtained in step c) is coupled with the polypeptide carrier a) by activating the COOH group in the derivative obtained in step 1c) in the form —COZ', in which Z' is a labile group known in peptide chemistry which enables b) a covalent amide bond to be produced with a free amino group of the polypeptide carrier.

Z' may be a known group in the state of the art, such as those described in Peptide Synthesis by Bodanszky, Y. S. Klausner and M. A. Ondetti, Second Edition (1976), John Wiley & Sons, in particular pages 85 to 136. As Z', the ($—N_3$) group, a halogen, especially bromine or chlorine, or an acyloxy group of the formula $R^5CO.O$ in which $R^5$ is an aliphatic or aromatic radical such as, for example, a $C_1$-$C_4$ alkyl, an alkoxy group, preferably a $C_1$-$C_4$ alkoxy group, or an aryloxy group, methanesulphonyloxy, tosyloxy or benzenesulphonyloxy, an imidazolyl radical or the radical of a N-acylhydroxylamine derivative may be mentioned; for example, Z' may be a succinimidoxy, phthalimidoxy or benzotriazolyloxy. The preferred examples are N-acylhydroxylamine groups, especially the N-hydroxysuccinimide esters prepared using 1-cyclohexyl-3-(2-morpholinoethyl) -carbodiimide metho-p-toluenesulphonate or 1,3-dicyclohexyl-carbodiimide or via a mixed anhydride such as those obtained using isobutyl chloroformate.

When Z' is an imidazolyl radical, it may be prepared using a di-imidazole carbonyl radical and when Z' is $R^5CO.O$ in which $R^5$ is a $C_1$-$C_4$ alkyl, especially ethyl and isobutyl, it may be prepared using a 1-ethoxycarbonyl-2-ethoxy-1,2-dihydroquinoline and isobutyl chloroformate respectively.

The reaction is carried out as follows. The hydrazide is dissolved in a solvent such as MeOH in an acid medium, for example 1 N HCl, the solution is cooled and a nitrite such as sodium nitrite is added, the pH is then adjusted with a weak base such as sodium bicarbonate and an acid azide is thus obtained which is extracted with a non-miscible solvent such as methylene chloride. After separation, the dried and concentrated azide is treated with the amine corresponding to the desired product (H—A—R'—CO2) and the crude product is separated from the reaction mixture and purified if necessary.

The amide obtained is separated from the reaction medium by any appropriate process.

The derivative containing a protected COOH group is then treated to remove the protection, for example it is subjected to hydrogenation in methanol in the presence of 10% palladium charcoal.

Finally, the coupling with the protein is preferably effected in an aqueous medium at a temperature of between 5° C. and 25° C., for example at room temperature, and at a pH between 7.5 and 9.5, preferably 8 and 9. The coupling takes place on a free amino group of the vehicle protein, for example an amino group of a lysine radical.

Finally, the invention also relates, by way of an intermediate product used in the process according to claim 9, a C-3 vinca derivative carrying in the C-3 position a detergent chain of at least 7 aliphatic carbon atoms, the said chain being substituted at its end by the COZ' group, from step 2a) of the process of claim 9.

The invention also relates to the use of the conjugates as a medicament and to pharmaceutical compositions incorporating these conjugates and containing pharmaceutically acceptable excipients, carriers or vehicles.

The compounds according to the present invention in fact have antineoplastic properties which make them particularly valuable in the treatment of malignant neoplasias such as leukemias, generalized Hodgkin's disease, certain lymphomas, sarcomas or carcinomas in particular.

Other characteristics and advantages of the present invention will be evident in the light of the following examples illustrated by FIGS. 1 to 3 as described below.

EXAMPLE 1

Preparation of N-(11-carboxyundecyl)-4-deacetylvinblastine-3-carboxamide (compound No. 2060)

The process is described with reference to the synthesis scheme I below.

A) N-(11-carbobenzyloxyundecyl)-4-deacetyl-vinblastine-3-carboxamide (3).

0.600 g (0.78 millimole) of the hydrazide of deacetylvinblastine (1), the preparation of which has been described in (CONRAD et al. J. Med. Chem. 22,391 (1979)), is dissolved in a mixture containing 12 ml of methanol and 36 ml of 1N HCl. The solution is cooled to 0° C. and 0.123 g (1.78 millimoles) of dry NaNO$_2$ is then added in a single portion and with stirring. After 13 minutes, the pH of the solution is adjusted to 8.5 with a cold saturated solution of NaHCO$_3$.

The acid azide of deacetylvinblastine is extracted rapidly with 4×15 ml of CH$_2$Cl$_2$ and then washed with a saturated solution of NaCL.

The extracts are dried over Na$_2$SO$_4$ and concentrated to a volume of 20 ml. 0.354 g (1.16 millimoles) of benzyl 12-aminododecanoate (2) are added to the CH$_2$Cl$_2$ solution and the solution is stirred for 2 hours at room temperature. Thin layer chromatography reveals a major component (Rf=0.46; methanol: methylene chloride 5:95).

The solvent is evaporated and the residue chromatographed on silica using a mixture of ethyl acetate: methanol (96:4) as the eluent. The appropriate fractions are combined and the solvents removed to obtain 450 mg of N-(11-carbobenzyloxyundecyl)-4-deacetylvinblastine-3-carboxamide (yield: 55%), with the following physical characteristics:

Rf: 0.46 (silica, CH$_2$Cl$_2$: CH$_3$OH 95:5)

MS: mass spectroscopy (DCI, isobutane) 1043 (M$^+$+1), 1057 (M$^+$+14+1), 1025, 1011, 999, 985, 966, 951

NMR: (CDCl$_3$, 200 MHz): 9.52 (OH, 1H), 8.03 (NH, 1H), 7.51 (H,H4, H—12') (2H), 7.45-7.04 (aromatic compounds, 7H), 6.61 (H—12, 1H), 6.07 (H—9, 1H), 5.83 (H—14, H—15, 2H), 5.12 (CH$_2$—Ph, 2H), 4.19 (H—17, 1H), 3.96 (H—17 A', 1H), 3.77 (OCH$_3$, 3H), 3.58 (OMe, 3H), 3.35 (H—2), 2.79 (N—CH$_3$), 2,64 (H—21)

IR: (KBr, cm$^{-1}$) 3460, 2930, 2858, 1734, 1660, 1614, 1508, 1460, 1228, 740

Molecular formula: C$_{62}$H$_{83}$N$_5$O$_9$

Molecular weight: 1041.617.

B) N-(11-carboxyundecyl)-4-deacetylvinblastine-3-carboxamide (4)

A solution of 400 mg (0.38 millimole) of N-(11-carbobenzyloxyundecyl)-4-deacetylvinblastine-3-carboxamide (3)- in 25 ml of methanol is subjected to hydrogenation at room temperature and atmospheric pressure in the presence of a spatula tip of 10% palladium charcoal. After stirring for 15 hours, 2 ml of methanol saturated with NH$_3$ are added and the solution is filtered through Decalite. The filter is washed with 2×10 ml of methanol.

The filtrate is concentrated under vacuum. The residue obtained is then purified by chromatography on silica using a mixture of eluents made up of ether, methanol and aqueous 15N ammonia in a ratio of 50/49.5/0.5.

The appropriate fractions are combined and the solvents removed to obtain 307 mg (0.32 millimole) of N-(11-carboxyundecyl)-4-deacetylvinblastine-3-carboxamide. Yield: 84%.

After trituration in a mixture of ethyl acetate and petroleum ether, the product is obtained in the form of an amorphous white powder having the following physical characteristics:

Rf: 0.33 (silica, CH$_2$Cl$_2$: CH$_3$OH 90:10)

MS: (DCI) 952, 892, 809, 749, 709, 663, 651, 610, 598, 571

NMR: (CDCl$_3$, 200 MHz), 8.02 (NH, 1H), 7.52 (H-11, H-12, 2H), 6.49 (H-12, 1H), 6.07 (H-9, 1H), 5.81 (H-14-15, 2H), 4.15 (H-17, 1H), 3.77 (OMe, 3H), 3.58 (OMe, 3H), 3.33 (H-2), 2.79 (N-Me), 2.58 (H-21)

IR: (KBR, cm$^{-1}$) 3460, 2925, 2853, 1719, 1660, 1613, 1501, 1460, 1229.

Molecular formula: C$_{55}$H$_{77}$N$_5$O$_9$

Molecular weight: 951.57

The bis-methanesulfonate salt is prepared by dissolving N-(11-carboxyundecyl)-4-deacetylvinblastine-3-carboxamide (4)- (110 mg) in anhydrous ethanol and adding 2% ethanolic methanesulfonic acid. The solution is concentrated under vacuum. 3 ml of distilled water are added to the residue and the solution obtained is lyophilized to give 133 mg of the bis-methanesulfonate salt.

SYNTHESIS SCHEME I

Compound 2060 (4)

EXAMPLE 2

Conjugate between N-(11-carboxyundecyl)-4-deacetylvinblastine-3-carboxamide (4) and galactosylated human serum albumin A solution of isobutyl chloroformate (16 µl) in dry dioxane (2 mg) is added dropwise at 10° C., with stirring, to N-(11-carboxyundecyl)-4-deacetylvinblastine-3carboxamide (97 mg) and triethylamine (17 µl) dissolved in dioxane (80 ml). After stirring for 15 minutes, the organic mixture is transferred dropwise, with stirring, into 185 ml of a galactosylated human serum albumin solution (5.4 mg/ml) in a 0.15M phosphate buffer (pH 8.5).

The mixture is stirred at room temperature for 15 hours. It is then purified by filtering through G25 gel equilibrated with a 9% NaCl solution.

The excluded peak is recovered, filtered through Millipak 40 (0.22 µ), concentrated until a volume of 16 ml is obtained and sterilized.

The protein content is measured by the Lowry technique and the alkaloid content estimated by measuring the radioactivity.

The conjugate thus prepared contains 6.2 moles of N-(11-carboxyundecyl)-4-deacetylvinblastine-3-carboxamide per mole of galactosylated albumin.

Development of the technique for coupling compound 2060 ($V_3$-$(CH_2)_{11}$-COOH) to Ahgal It is advisable to obtain conjugates having the maximum medicament/carrier molar ratio while retaining the best possible yield of macromolecular carrier in monomer form.

Beyond a certain threshold in the drug/carrier molar ratio, polymerization of the carrier takes place very rapidly, rendering it unusable. It would seem that this polymerization affects the recognition characteristics of the protein.

| Ratio employed | | Ratio obtained | HPLC | | |
|---|---|---|---|---|---|
| moles vinca/ moles lysine | % dioxane | moles vinca/ moles AHgal | % Mono $7.10^4$ | % P.M. $15.10^4$ | % P.M. $67.10^4$ |
| 0.3 | 7.3 | 2 | 55 | 9 | 36 |
| 0.3 | 15 | 2.8 | 65 | 28 | 7 |
| 0.3 | 30 | 8 | 45 | 55 | — |
| 0.6 | 30 | 14.7 | 29 | 70 | 1 |
| 0.9 | 30 | 25 | 17 | 82 | 1 |

EXAMPLE 3

3.1 Chemotherapeutic activity on leukemia P 388

Tests to determine the antitumor activity of derivatives of VLB conjugates of Examples 1 and 2 were carried out on mice in the following way:

3.1.1. Activity parameters

Two activity parameters were used: the "I.L.S." parameter represents the prolongation of life as a percentage and in accordance with the following equation

$$I.L.S. \% = \left(\frac{T}{C} \times 100\right) - 100$$

T (in days) being the mean duration of life of the treated mice and C (in days) being the mean duration of life of the reference mice. The "long term survivors" parameter, the calculation in percentage of which was determined on day 60.

3.1.2. Intraperitoneal administration

Female $BDF_1$ mice were infected intraperitoneally on day 0 with $10^6$ cells of leukemia $P_{388}$. The following day compound 2060 was administered intraperitoneally.

| Product | Dosage mg/kg/day | No. of mice | ILS % | Survivors on day 60 | Remarks |
|---|---|---|---|---|---|
| 2060 | 25 | 7 | 82 | 0/7 | NaCl 9°/$_{oo}$ |
| | 45 | 7 | 186 | 0/7 | $H_2O$ |
| | 50 | 7 | 105 | 0/7 | NaCl 9°/$_{oo}$ |
| | 50 | 7 | 156 | 2/7 | $H_2O$ |
| | 75 | 7 | −38 | 0/7 | NaCl 9°/$_{oo}$ |

$$-2060 = V_3-(CH_2)_{11}-C\overset{\displaystyle O}{\underset{\displaystyle OH}{\diagup}}$$

The conjugate of derivate 2060 coupled to galactosylated human albumin (AHg) gave the following outstanding results.

Chemotherapeutic activity of 2060-AHg conjugate on leukemia P388 implanted intraperitoneally in female $BDF_1$ mice ($10^6$ cells intraperitoneally, treatment intraperitoneally on day 1)

| Exp. No. | Dosage of Vinca mg/kg | Dos. of Prot mg/kg | No. of mice | % ILS | Survivors on day 60 | Molar ratio | Conjugated batch | % Mono |
|---|---|---|---|---|---|---|---|---|
| 537 | 20 | 259 | 7 | >582 | 4/7 | 6.2 | 1166 | 59 |
| 543 | 20 | 318 | 7 | >689 | 4/7 | 5.1 | 1182 | 53 |
| 543 | 30 | 477 | 7 | 197 | 3/7 | 5.1 | 1182 | 53 |
| 537 | 40 | 517 | 7 | −31 | 0/7 | 6.2 | 1166 | 59 |
| 556 | 20 | 360 | 7 | 267 | 2/7 | 4.5 | 1205 | 57 |

3.2 - Chemotherapeutic activity on HepG2 hepatoma

Approximately 2 mm³ fragments of HepG2 hepatoma were implanted subcutaneously, bilaterally and dorsally, in shaven Balb/c female mice on day 0. When the tumors reached a given mass (about 500 mg), the treatment was administered intravenously. The development of the tumor masses was followed as a function of time. The tumor diameters were measured in order to determine the tumor mass using the equation:

$$\text{Mass (mg)} = \frac{L \text{ (mm)} \times l^2 \text{ (mm)}}{2} \text{ (on day } x\text{)}$$

L=length; l=width.

The ratios of the tumor masses on day X/tumor mass on the first day of treatment were plotted in a graph as a function of time (relative mass or RM/T).

The products administered are 9% NaCl for the controls and the 2060-AHgal conjugate in respective doses of 15, 20 and 25 mg/kg. The graph shown in FIG. 1 shows the mean relative masses as a function of time. The treatment was administered in 5 intravenous injections on days 26, 33, 40, 47 and 54 respectively.

Figure 1:
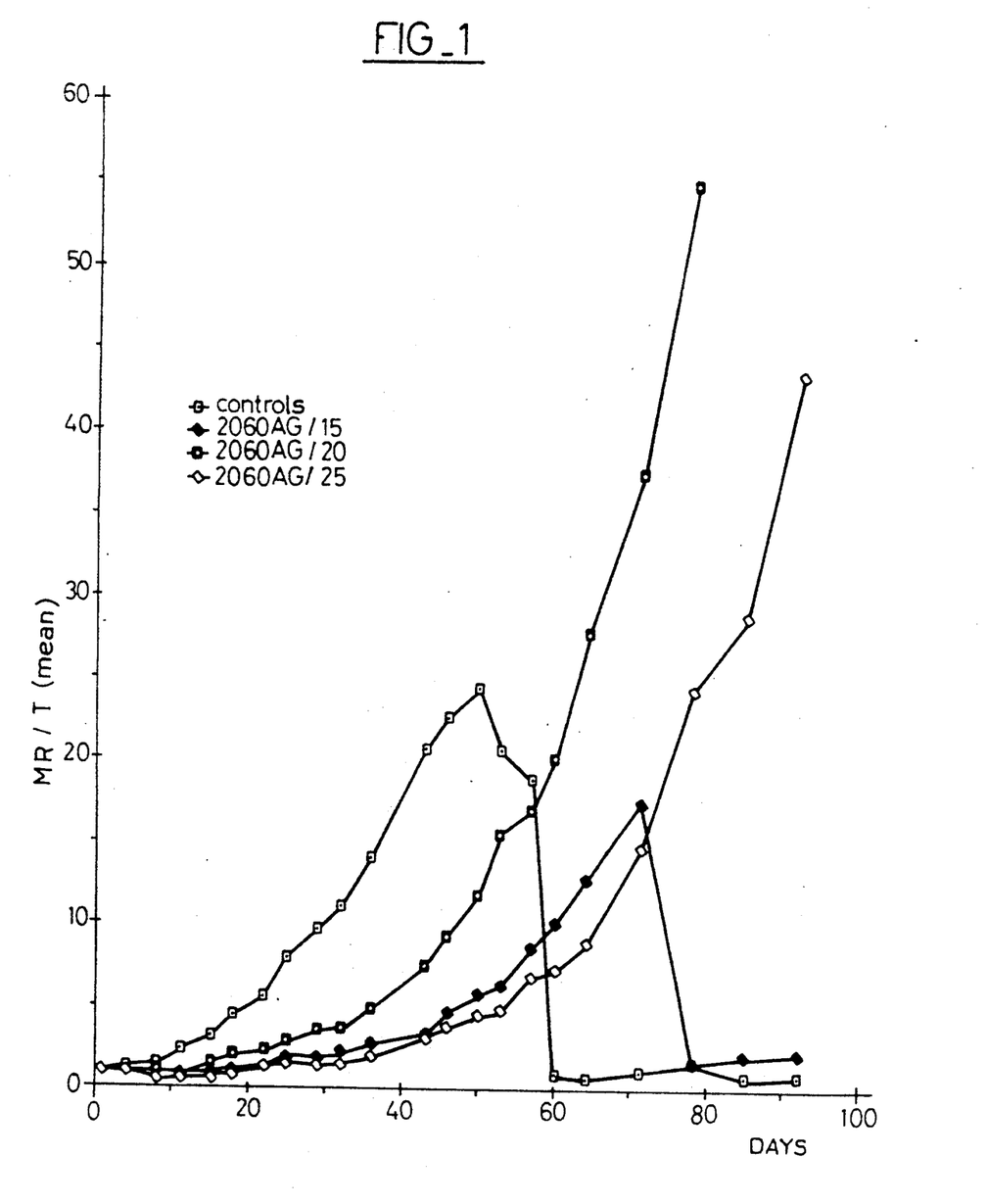
FIG. 1 represents the relative tumor mass as a function of time for HepG$_2$ hepatomas treated with the conjugate 2060 AHgal in various dosages.

The results in FIG. 1 show a partial inhibition of growth of significant tumors for three dosages evaluated.

For the HepG2 a very great discrepancy in the tumors is observed and sometimes a tumor of a specific mass stops developing at a given point in time. This is observed with the control series. In fact, the mean of the relative masses of the controls develops to reach 25 times the starting value. The mice with the largest tumors die and a fall in the mean is then observed. The latter drops back to a very low value corresponding to a hepatoma which has ceased to develop. In fact, usually the mean should drop back to 0.

With regard to the effect of the conjugate, a very clear inhibition of the development of the tumor masses is observed. After treatment is ceased, a recrudescence of the tumors is observed. The survival of the treated animals is also greater than that of the controls.

EXAMPLE 4

4.1 - Stability of the 2060-AHgal conjugate in serum

The 2060-AHgal conjugate was incubated at 37° C. in the presence of 80% of the human serum or of 9% NaCl (physiological serum).

After various incubation times T, the non-degraded proteins were precipitated, after the addition of 5 mg of serum albumin, by two volumes of acetonitrile.

After incubating the samples at 4° C. for one hour, these were centrifuged and the radioactivity of the supernatant liquor was estimated by counting an aliquot portion by liquid scintillation.

The soluble radioactivity is a measure of the digestion of the conjugate.

The values shown in Table I below represent the percentage of soluble radioactivity (tritiated vinca).

Figure 2:
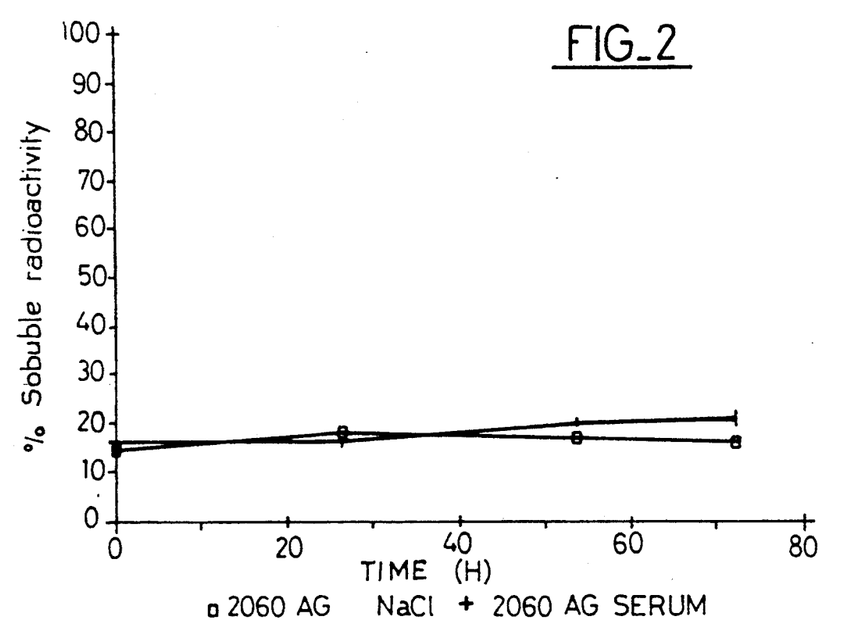
FIG. 2 represents the stability curve in serum of a 2060 AHgal conjugate according to the invention.

The results in Table I, also reproduced in FIG. 2, establish the good stability of the conjugate in the serum.

4.2 - Digestion of the 2060-AHgal conjugate by lysosomal enzymes

The conjugate was incubated at 37° C. in the presence of 5 mM cysteine, 40 mM acetate buffer and lysosomal enzymes (T.S.) or water.

After various incubation times T, the non-degraded proteins were precipitated, after the addition of 5 mg of serum albumin, by two volumes of acetonitrile.

After incubating the samples at 4° C. for 40 minutes and centrifuging at 3000 rpm for 40 minutes, the radioactivity of the supernatant liquor was estimated by counting an aliquot portion by liquid scintillation. The soluble radioactivity is a measure of the digestion of the conjugate.

Figure 3:
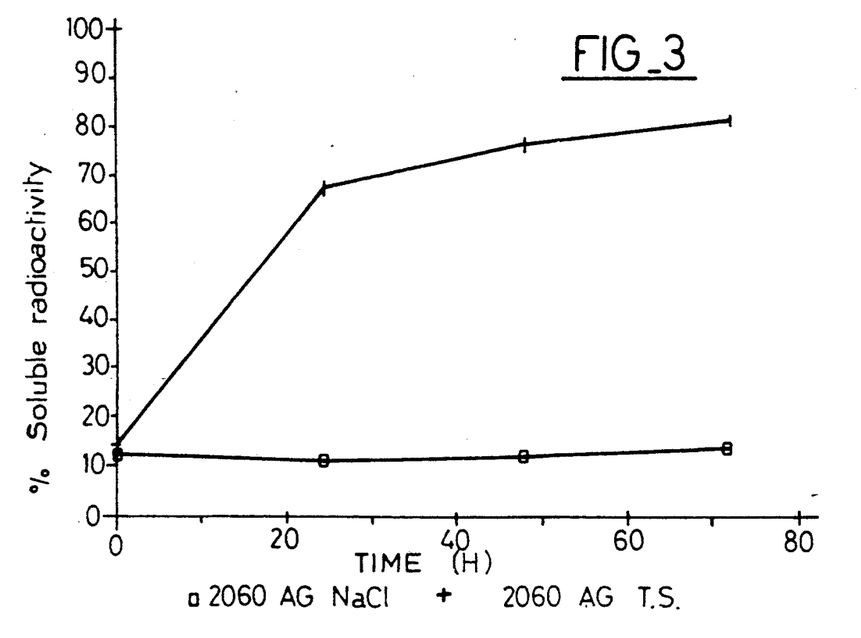
FIG. 3 represents the digestion curve of the same conjugate for lysosomal enzymes.

The percentage of soluble radioactivity shown in Table I and in FIG. 3 shows that about 80% of the conjugates has been digested by the lysosomal enzymes (T.S.)

TABLE 1

| $V_3$—$C_{12}$—AHgal (2060-AG) | | | | |
|---|---|---|---|---|
| STABILITY 80% SERUM HUMAN | | | DIGESTION TS | |
| TIME (H) | NACL 9% | SERUM | $H_2O$ | TS |
| 0 | 14° | 12.2 | 12.3 | 14.3 |
| 24.3 | 16.8 | 8 | 11.2 | 67.8 |
| 47.55 | 16.6 | 9 | 12.3 | 77.3 |
| 71.5 | 13.3 | 18.4 | 14.1 | 82.8 |

EXAMPLE 5

Coupling of N-(11-carboxyundecyl)-4-deacetylvinblastine-3-carboxamide to monoclonal antibody (IgG CTM01 type)

A solution of isobutyl chloroformate (2.8 μl) in dry dioxane (0.5 ml) is added dropwise at 10° C., with stirring, to N-(11-carboxyundecyl)-4-deacetylvinblastine-3-carboxamide (16 mg) and triethylamine (2.6 μl) dissolved in 1 ml of dioxane. After stirring for 15 minutes, the organic mixture is transferred dropwise with stirring, into 20 ml of a monoclonal antibody solution (8.5 mg P/ml) in a 0.1M phosphate buffer of pH 8.5.

The mixture is stirred at room temperature for 1 night. It is then purified by filtration through Sephadex G25 gel equilibrated in a solution of 9% NaCl of pH 7.5. The peak excluded is collected, concentrated by ultrafiltration and sterilized.

The protein content is measured by the Lowry method and the alkaloid content is estimated by measuring the radioactivity.

The conjugate thus prepared contains 1 mole of N-(11-carboxyundecyl)-4-deacetylvinblastine-3-carboxamide per mole of monoclonal antibody.

We claim:

1. A conjugate of a vinca (indole-dihydroindole) derivative having a formula in which
$R_1$ and $R_2$ together represent (1) —Et and —OH or (2) —H and —Et;
$R_3$ represents —OH or A represents —NH— or a divalent radical of an amino acid found in a protein, wherein said divalent radical of said amino acid is terminated by R' represents an aliphatic hydrocarbon radical having at least 7 aliphatic carbon atoms; and
—NH—P represents a radical derived from $NH_2P$, wherein $NH_2P$ represents a macromolecular carrier of polypeptide origin in which said $NH_2$ represents a free amino group.

2. The conjugate according to claim 1, wherein $R_3$=OH and A=—NH—.

3. The conjugate according to claim 1, wherein $R_1$ and $R_2$ together represent —Et and —OH and $R_4$=Me.

4. The conjugate according to claim 1 wherein —A—R— is —NH—$(CH_2)_{11}$—, —NH—$(CH_2)_{17}$— or —NH—$(CH_2)_7$—CH=CH—$(CH_2)_8$.

5. The conjugate according to claim 1, wherein said macromolecular carrier is selected from proteins, neoglycoproteins, and fragments thereof.

6. The conjugate according to claim 5, wherein said macromolecular carrier is bovine serum albumin, galactosylated human albumin, or a growth factor.

7. The conjugate according to claim 6, wherein said growth factor is epidermal growth factor.

8. The conjugate according to claim 1, wherein said macromolecular carrier is an IgG immunoglobulin or a fragment thereof.

9. The conjugate according to claim 8, wherein said immunoglobulin is a monoclonal antibody.

10. The conjugate of claim 1, wherein said macromolecular carrier is galactosylated human serum albumin.

11. Pharmaceutical composition containing a conjugate according to claim 1 as the active ingredient.

12. Composition according to claim 11, wherein said composition is in an injectable form.

13. A pharmaceutical composition containing a conjugate according to claim 1 as the active ingredient.

14. A composition according to claim 13, wherein said composition is in injectable form.

15. A pharmaceutical composition containing a conjugate according to claim 6 as the active ingredient.

16. A composition according to claim 15, wherein said composition is in an injectable form.

* * * * *